United States Patent [19]

Martin

[11] Patent Number: 5,207,650
[45] Date of Patent: May 4, 1993

[54] INFUSION CATHETERS

[75] Inventor: Geoffrey S. Martin, Mississauga, Canada

[73] Assignee: Med-Pro Design, Inc., Mississauga, Canada

[21] Appl. No.: 854,023

[22] Filed: Mar. 19, 1992

[30] Foreign Application Priority Data

Mar. 20, 1991 [CA] Canada ................................ 2038676

[51] Int. Cl.⁵ ............................................. A61M 5/00
[52] U.S. Cl. .................................................. 604/173
[58] Field of Search ............... 604/173, 264, 280, 284

[56] References Cited

U.S. PATENT DOCUMENTS

| | | |
|---|---|---|
| 4,072,146 | 2/1978 | Howes . |
| 4,214,593 | 7/1980 | Imbruce et al. . |
| 4,385,631 | 5/1983 | Uthmann ............... 604/284 |
| 4,406,656 | 9/1983 | Hattler et al. . |
| 4,543,087 | 9/1985 | Sommercorn et al. ......... 604/264 X |
| 4,838,881 | 6/1989 | Bennett . |
| 4,894,057 | 1/1990 | Howes . |
| 4,995,865 | 2/1991 | Gahara et al. ............... 604/280 X |
| 5,009,636 | 4/1991 | Wortley et al. ............... 604/280 X |
| 5,135,599 | 8/1992 | Martin et al. ............... 604/280 X |

Primary Examiner—John J. Wilson
Assistant Examiner—Jeffrey A. Smith
Attorney, Agent, or Firm—Rogers & Scott

[57] ABSTRACT

An infusion catheter is provided having a main body including a continuous generally round cross-section about a longitudinal axis. The body has proximal and distal ends. A tip section has a round cross-section and is smaller in cross-section than the main body and ends in a tip. The tip section is attached to the distal end of the main body at a transition portion which tapers smoothly from the main body to the tip section. The main body and tip section define a primary lumen extending from the proximal end of the body to the tip and the lumen is continuous. This lumen has a longitudinal axis offset from that of the main body and the main body further includes a pair of side-by-side secondary lumens terminating at respective side openings in the main body. A first of these openings is adjacent the transition portion and the second is spaced from the transition portion. Plug material is provided in the main body between said second opening and the transition portion. The catheter can have more than two secondary lumens. The catheter is made using a process to align the body and tip section while heat and pressure cause the formation of the transition portion.

6 Claims, 3 Drawing Sheets

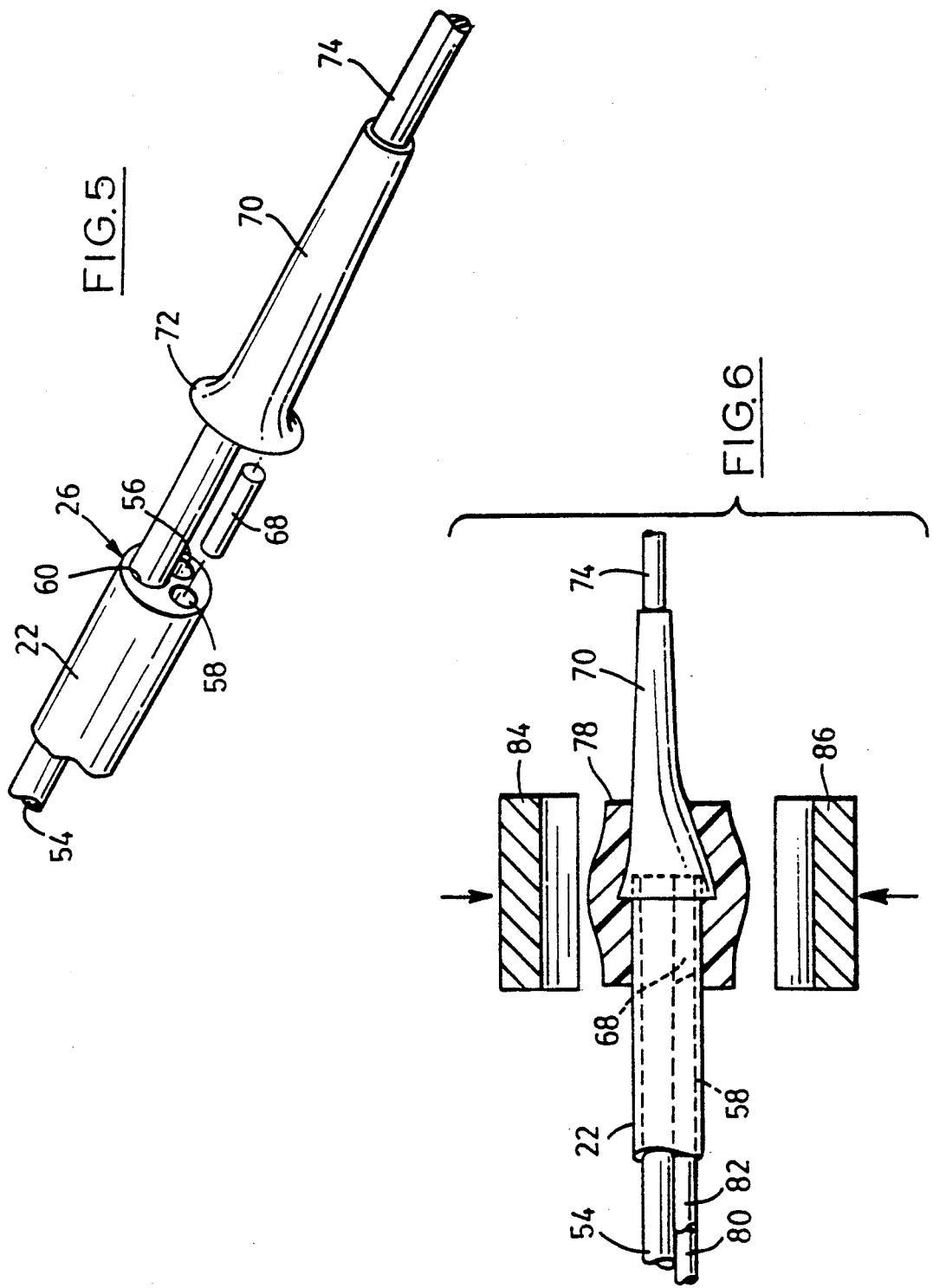

INFUSION CATHETERS

BACKGROUND OF THE INVENTION

This invention relates to an infusion catheter for use in supplying fluids such as nourishment, drugs, blood, and colloids simultaneously to different locations in a patient's vein, and more particularly to such an infusion catheter which can be inserted using a guidewire of the Seldinger type.

U.S. patent Ser. No. 4,072,146 which issued on Feb. 7, 1978 to Randolph M. Howes teaches the use of a single catheter providing three distinct lumens for infusion at different locations along the length of a vein containing the catheter. The Howes patent indicates that prior to the application for that patent, venous catheter devices each provided a single lumen which could be used for one purpose only. These purposes included administering drugs or I.V. feeding, monitoring venous pressures or withdrawing blood samples. The disadvantage of this approach is that a catheter must be provided for each one of these functions. Further, the catheter can not be used other than for the single function because it is undesirable and contraindicated to mix many of the drugs and I.V. fluids prior to their entering the blood stream. Also, withdrawal of blood samples can not be performed through a catheter that has previously supplied drugs.

Because it was common in intensive care situations to administer a plurality of drugs simultaneously, there was a need to provide a structure capable of doing this without requiring multiple insertions with the resulting associated trauma. This was particularly true in situations where patients required insertion of catheter devices simultaneously in major veins such as the external or internal jugular, subclavian, cephalic, femoral or saphenous veins. This multiple insertion could result in considerable risk to the patient, discomfort, and possible bleeding and infection. Further, because it is necessary to move the location of the catheters periodically, new punctures must be made with resulting further discomfort and possible complications.

The Howes patent approached the problem by providing a single catheter with multiple lumens which terminated at different locations along the length of the catheter. As a result, when the catheter was inserted in a vein it would provide access to different locations in the vein. The improved venous catheter device was used together with a needle as a venipuncture device, or apart from a needle in which case a vein was exposed and partially transected for direct insertion of the catheter.

To achieve these ends, Howes provided structures of several types. The first was an outer sheath containing individual tubes to define the lumens and they had to be attached to the sheath where infusion was to take place. An alternative was to provide an extrusion having several lumens and which again opened in the side wall of the catheter. In both cases the distal or leading end of the catheter was simply cut from the sheath or the extrusion to provide an opening for one of the lumens.

While the Howes structure has opened the way for an approach using a single catheter with multiple lumens, it has not addressed some of the fundamental problems existing in the art of catheter insertion.

First of all it is evident that a catheter, no matter how many lumens it contains, must have minimal cross-section in order to interfere as little as possible with the flow of blood in the vein, and also to facilitate insertion. Consequently it is necessary to define the cross-section in such a way that the lumens are contained as efficiently as possible in a minimal crosssection while at the same time providing sufficient rigidity and compression resistance that the catheter will have minimal likelihood of kinking or collapsing in use. Further, modern catheter placement commonly dictates the use of the Seldinger technique which is a technique for guiding a catheter over a wire. This minimizes trauma and, with suitable catheter shape, can dilate the body tissue as it is inserted thereby ensuring a good seal and minimal bleeding. Howes structure is not capable of being inserted this way and is in fact designed specifically to be inserted either with an oversized needle, which of course would result in a enlarged opening in the body tissue, or by an incision which would have similar results.

A further consideration when inserting catheters into veins is the rigidity of the tip section. A softer tip is desirable so that it will not tend to apply a load to the wall of the vein while it is in position. Consequently, a reduced diameter at the tip together with some reduction in the hardness of the material is desirable.

In an attempt to improve over the structures shown in U.S. patent Ser. No. 4,072,146, Howes adopted a structure shown in U.S. patent Ser. No. 4,894,057 which issued on Jan. 16, 1990. However this structure, although an improvement over that shown in U.S. Pat. No. 4,072,146, continues to use the same form of insertion as in the prior patent. This may not be readily apparent by reading U.S. Pat. No. 4,894,057 but is is clear when it is related to the earlier patent that the same type of insertion must be used. If the structure shown in U.S. Pat. No. 4,894,057 were to be moved over a guidewire, then the ends of the lumens which terminate short of the tip would cut into body tissue and become occluded. This is clearly dangerous and it is evident that the structure must also be inserted either within a needle or by a cut down technique.

The inherent disadvantages of the Howes structures are detrimental to the use of a multiple lumen catheter for multiple infusion.

It is accordingly an object of the present invention to provide a multiple lumen infusion catheter having a minimal cross-section and which can be inserted using the Seldinger technique to minimize trauma and provide an efficient insertion with minimal bleeding.

SUMMARY OF THE INVENTION

An infusion catheter is provided having a main body including a continuous generally round cross-section about a longitudinal axis. The body has proximal and distal ends. A tip section has a round cross-section and is smaller in cross-section then the main body and ends in a tip. The tip section is attached to the distal end of the main body at a transition portion which tapers smoothly from the main body to the tip section. The main body and tip section define a primary lumen extending from the proximal end of the body to the tip and the lumen is continuous. This lumen has a longitudinal axis offset from that of the main body and the main body further includes a pair of side-by-side secondary lumens terminating at respective side openings in the main body. A first of these openings is adjacent the transition portion and the second is spaced from the transition portion. Plug material is provided in the main body between said second opening and the transition portion.

The catheter can have more than two secondary lumens.

The catheter is made using a process to align the body and tip section while heat and pressure cause the formation of the transition portion.

BRIEF DESCRIPTION OF THE DRAWINGS

A preferred embodiment of the invention is to be described with reference to the following drawings, in which:

FIG. 5 is a diagrammatic perspective view illustrating one of the steps used in making the catheter; and FIG. 6 is a diagrammatic view, partly in section of another step in the manufacture.

As seen in FIG. 1 a catheter 20 is provided having a main body 22 extending between a proximal end indicated generally by the numeral 24 and a distal end, again indicated generally by a numeral, in this case 26. The distal end meets a tip section 28 which extends between the transition portion 30 where the tip section meets the main body 22, and a tip 32.

Figure 1:
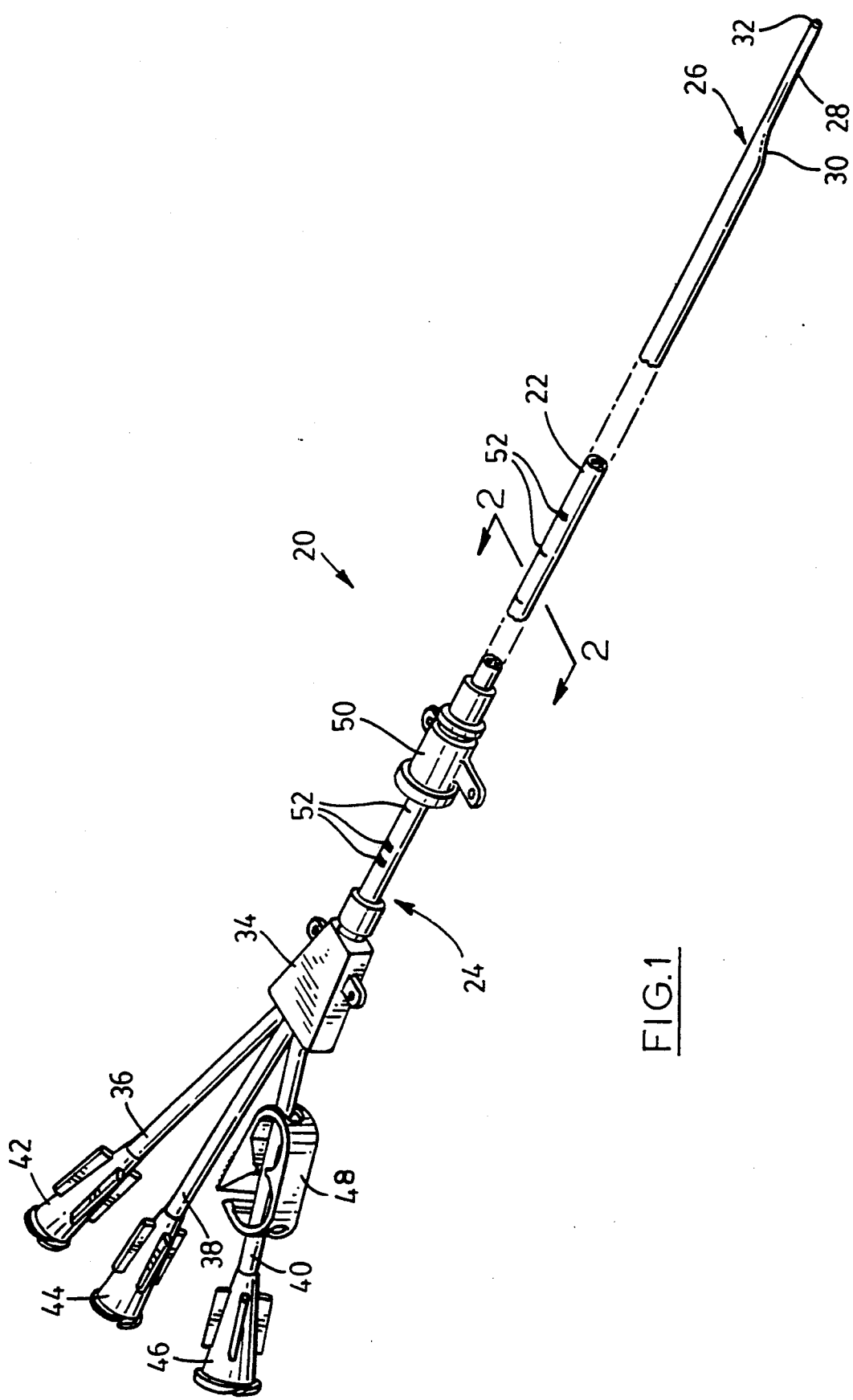
FIG. 1 is an isometric view looking generally from the distal end of a catheter according to the preferred embodiment of the invention.

At the proximal end of the body 22, a junction 34 provides connnection for three lumens contained in the main body 22 (as will be described with reference to FIG. 2). The junction 34 connects three flexible tubes 36, 38 and 40 which terminate in respective luer connectors 42, 44, 46. Each of the tubes 36, 38 and 40 will have a closure device such as that shown at 48 on tube 40. These are conventional fittings.

The main body 22 carries a removable wing structure 50 for attachment to the patient in conventional fashion. The wing structure is flexible and slit longitudinally on the underside as drawn so that it can be removed by tearing it off the body 22. The body also carries markings 52 graduated to indicate the position of tip relative to the outer skin surface of the patient.

It will be seen in FIG. 1 that the tip section 28 is offset with respect to the main body 22. Nevertheless it extends longitudinally with respect to the main body and the importance of this will be described with reference to the subsequent drawings.

Figure 2:
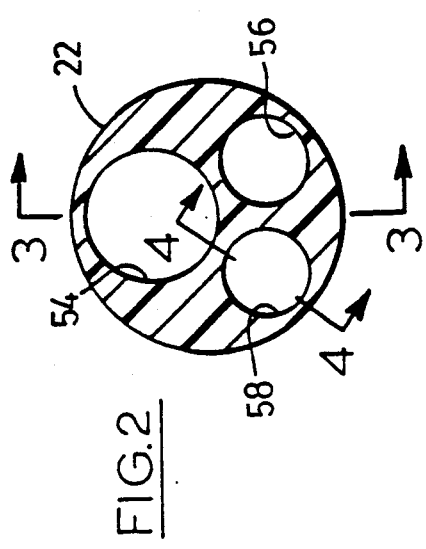
FIG. 2 is a cross-sectional view on line 2—2 of FIG. 1 drawn to a larger scale and illustrating the arrangement of three lumens in the catheter.

As seen in FIG. 2, the main body 22 of the preferred embodiment has a smooth generally circular outer surface which is continuous along the length of the main body. The main body contains a primary lumen 54 which is slightly larger in diameter than a pair of side-by-side secondary lumens 56, 58. The three lumens are contained within the main body and are separated so that they will not interfere with one another. There is sufficient material provided between the lumens that the catheter will resist buckling and the round sections of the lumens provide sufficient strength that there is little likelihood under normal conditions that there will be difficulties with collapsing of the walls.

Figure 3:
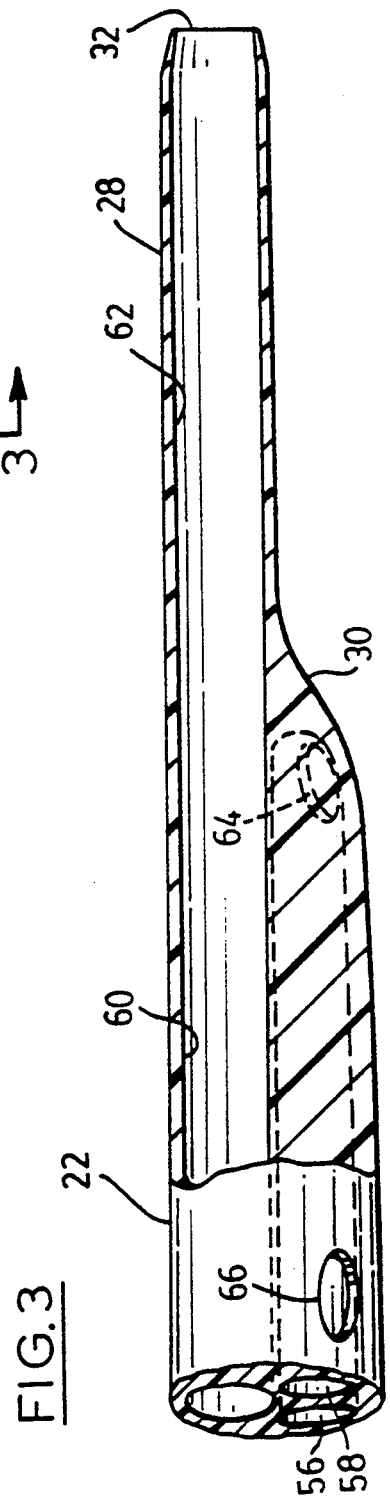
FIG. 3 is a diametric cross-sectional view of the catheter in the region of a tip section and transition portion.

The primary lumen 54 is slightly larger because this is the lumen which will accomodate a guide wire for insertion. As seen in FIG. 3, the lumen 54 includes a portion 60 contained within the main body 22 and extending continuously into extension 62 formed in the tip section 28. There is alignment between portion 60 and extension 62 along a longitudinal axis for smooth movement along the guide wire and of course initial insertion of the guide wire through this lumen. Also, this longitudinal axis is offset with respect to the corresponding axis of the main body. This assists in ensuring that these lumens are contained in as small a cross-section as possible without undue sacrifice of resistance to buckling and radial collapse. As a result of this, the secondary lumens must be contained to the sides of the primary lumen and the main body must have a transition to the tip section 28 while maintaining the alignment of the primary lumens. This is provided at transition portion 30 where the tip section is blended into the main body as will be described with reference to the subsequent drawings. For the moment, it is sufficient to understand that material is provided to create a tapered surface at the transition portion which converges towards the tip section to provide a ramp effect to facilitate dilating body tissue as the catheter moves over the guide wire and into the body tissue.

As also seen in FIG. 3, the lumen 56 (shown in broken outline) terminates at the transition portion 30 in an opening 64 providing access from this lumen to the vein when the catheter is in place. A similar opening 66 in lumen 58 provides further access spaced along the length of the catheter to minimize the risk of mixing liquids flowing through these lumens. A similar spacing is provided between the tip 32 which is the end of lumen extension 62 and the opening 64.

Figure 4:
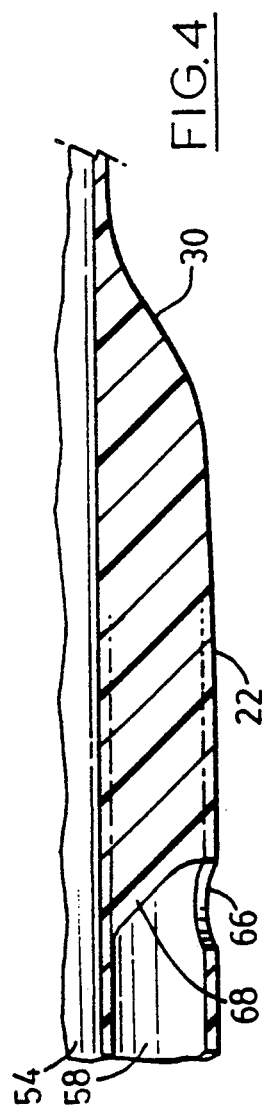
FIG. 4 is a sectional view similar to FIG. 3 and drawn diametrically through one of a pair of secondary lumens.

FIG. 4 illustrates the use of plug material 68 which is positioned in the lumen 58 before the opening 66 is made and prior to formation of the transition portion 30. After manufacture, the plug material is partly blended through a change of state in the material so that it effectively becomes one with the transition portion and part of the main body of the catheter. To illustrate this, the plug material is shown with a ghost outline around it indicating that there is no real transition. During manufacture of course the plug material can be positioned using adhesive or any suitable material to keep it in place and then the opening 66 is made later to ensure that it is positioned adjacent the plug material to minimize dead spaces in the catheter.

The method of manufacture of the preferred embodiment will now be described with reference to FIGS. 5 and 6. As seen in FIG. 5, a tip section preform 70 consists of a short tubular section of material which has been deformed at one end to create a flare 72 sufficiently large to engage over the distal end 26 of the main body 22. The internal diameter of the preform 70 matches that of lumen 54 (FIG. 2) so that a stainless steel rod 74 can be engaged snugly in the main portion 60 of the primary lumen and then in the preform 70. As seen in FIG. 5, this step is accompanied by the engagement of plug material 68 in lumen 58 and this is engaged until the outer end of the plug material is flush with the distal end 26.

Next, the preform 70 is slipped over the rod 74 into the position shown in FIG. 6. A flexible and heavy silicon sleeve 78 is pushed over the ends of the main body 22 and preform 70, and further rods 80, 82 are engaged in the respective lumens 56, 58 (FIG. 5). The rod 80 is engaged to the end of the main body 22 whereas the rod 82 is engaged until it touches the plug material 68. With all of these parts in position, heat is applied to the silicon sleeve 78 by a pair of copper jaws 84, 86 which are brought into engagement to also apply peripheral pressure to the materials while heat flows to soften and transform the materials into the transition portion 30 shown in FIG. 3. Once this is achieved, the structure is cooled and the rods removed before the tip 32 is tapered slightly (as indicated in FIG. 3) using conventional methods.

After the operations described with reference to FIGS. 5 and 6, openings 64, 66 are drilled into the catheter. Finally the connections are made at the proximal end of the main body to complete the structure.

The result of this manufacturing technique is that although the lumen containing the rod 74 is offset from the central axis of the main body 22, there is nevertheless a continuous smooth lumen without misalignment provided for the guidewire which is aligned between the portion 60 and extension 62 (FIG. 3). Further, the use of the method of manufacture ensures that there is a smooth transition portion 30 tapering outwardly towards the tip and providing for dilation of body tissue during insertion.

In a typical structure the main body has an outside diameter of 2.3 millimeters (0.091 inches) and defines a primary lumen of 0.96 millimeters (0.038 inches) and secondary lumens of 0.76 millimeters (0.030 inches). The material is polyurethane and the main body and tip sections have respective diameters of 2.3 millimeters (0.091 inches) and 1.65 millimeters (0.065 inches). If preferred the material of the preform 70 can be of a different durometer than that of the main body 22. This is useful for instance in forming the catheter with a very flexible tip to minimize risk of damage to a vein after insertion.

It will be evident that the catheter can take a variety of forms including having more than two secondary lumens and component tip sections of multiple hardness values. These and other variations are within the scope of the invention as claimed.

I claim:

1. An infusion catheter comprising:
   a main body having a continuous generally round cross-section about a longitudinal axis and having proximal and distal ends;
   a tip section having a round cross-section and being smaller in cross-section than the main body and ending in a tip;
   a transition portion connecting the tip section to said distal end and tapering smoothly from the main body to the tip section;
   the main body and tip section defining a primary lumen extending from said proximal end to the tip, the lumen being continuous where the main body meets the tip section and having a longitudinal axis offset from that of the main body;
   the main body further including a pair of side-by-side secondary lumens terminating at respective side openings in the main body, a first of these openings being adjacent the transition portion and the second being spaced from the transition portion;
   plug material in the main body between said second opening and the transition portion; and
   a junction at said proximal end and three flexible tubes connected for fluid flow to the respective lumens by the junction.

2. A catheter as claimed 1 in which the tip section is of a different durometer from that of the main body.

3. A catheter as claimed in claim 2 in which the tip section is very flexible sufficient to minimize the risk of damaging a vein after insertion.

4. An infusion catheter having at least three lumens for use in providing access in a vein to different locations spaced longitudinally in the vein, the catheter comprising:
   a main body having a smooth outer surface and a substantially constant cross-section about a longitudinal axis and defining a portion of a primary lumen and a plurality of secondary lumens separated from one another and from said primary lumen, the secondary lumens extending axially of the body side-by-side and in parallel with one another, the body having proximal and distal ends and the primary lumen being offset with respect to the longitudinal axis of the main body;
   a tip section extending axially from said distal end about said longitudinal axis and terminating at a tip, the tip section being of a smaller cross-section than the main body and defining an extension of said portion of the primary lumen completing the primary lumen which terminates at said tip the primary lumen being continuous as the lumen extends from said portion to said extension to facilitate the use of a guidewire in this lumen during insertion procedures;
   a transition portion where the main body meets the tip section, the transition portion blending the distal end of the main body into the tip section as a gradual taper converging towards said tip to provide a smooth dilating surface to minimize trauma during insertion;
   the secondary lumens terminating at spaced intervals along the main body, one of the secondary lumens terminating adjacent the transition portion;
   plug material contained in the main body to terminate those of the secondary lumens not terminating at the transition portion whereby the primary lumen provides for insertion in a vein over a guidewire and this lumen and the secondary lumens then provide access at discrete locations along the vein to minimize the risk of mixing liquids infused through the different lumens; and
   a junction at said proximal end and three flexible tubes connected for fluid flow to the respective lumens by the junction.

5. A catheter as claimed 4 in which the tip section is of a different durometer from that of the main body.

6. A catheter as claimed in claim 5 in which the tip section is very flexible sufficient to minimize the risk of damaging a vein after insertion.

* * * * *

REEXAMINATION CERTIFICATE (3139th)

United States Patent [19]

Martin

[11] B1 5,207,650

[45] Certificate Issued Feb. 25, 1997

[54] INFUSION CATHETERS

[75] Inventor: Geoffrey S. Martin, Mississauga, Canada

[73] Assignee: Med-Pro Design, Inc., Mississauga, Canada

Reexamination Request:
No. 90/003,936, Aug. 28, 1995

Reexamination Certificate for:
Patent No.: 5,207,650
Issued: May 4, 1993
Appl. No.: 854,023
Filed: Mar. 19, 1992

[30] Foreign Application Priority Data

Mar. 20, 1991 [CA] Canada ................................ 2038676

[51] Int. Cl.⁶ .................................................... A61M 5/00
[52] U.S. Cl. .................................................... 604/173
[58] Field of Search ............................ 604/173, 264, 604/280, 284

[56] References Cited

U.S. PATENT DOCUMENTS 5,167,623  12/1992  Cianci et al. .
5,221,255  6/1993  Mahurkar et al. .

*Primary Examiner*—Gene Mancene

[57] ABSTRACT

An infusion catheter is provided having a main body including a continuous generally round cross-section about a longitudinal axis. The body has proximal and distal ends. A tip section has a round cross-section and is smaller in cross-section than the main body and ends in a tip. The tip section is attached to the distal end of the main body at a transition portion which tapers smoothly from the main body to the tip section. The main body and tip section define a primary lumen extending from the proximal end of the body to the tip and the lumen is continuous. This lumen has a longitudinal axis offset from that of the main body and the main body further includes a pair of side-by-side secondary lumens terminating at respective side openings in the main body. A first of these openings is adjacent the transition portion and the second is spaced from the transition portion. Plug material is provided in the main body between said second opening and the transition portion. The catheter can have more than two secondary lumens. The catheter is made using a process to align the body and tip section while heat and pressure cause the formation of the transition portion.

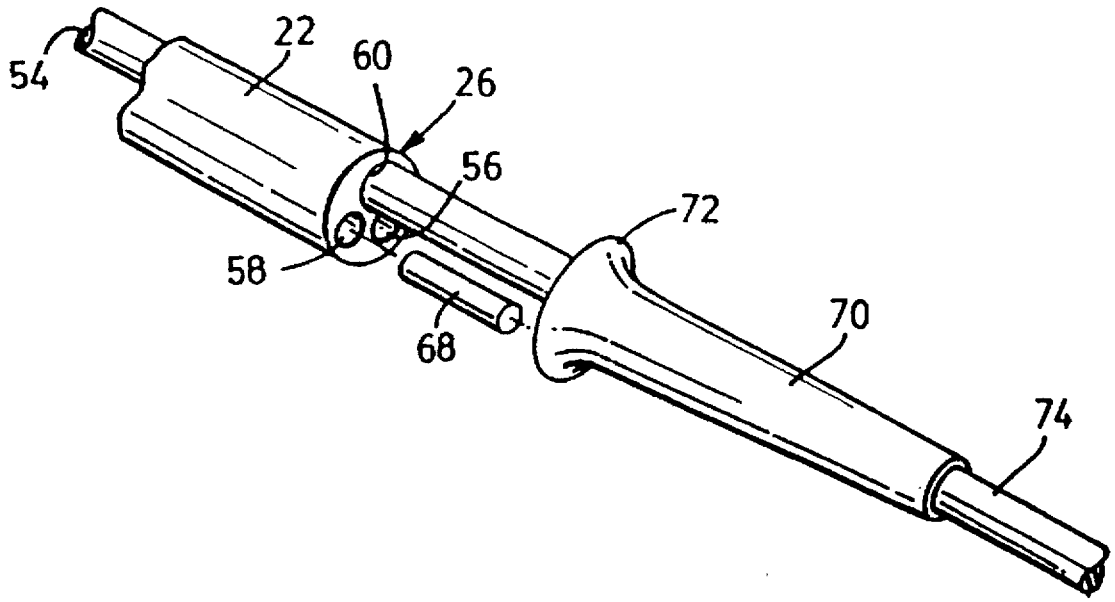

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

* * * * *